(12) United States Patent
Takase et al.

(10) Patent No.: US 6,716,159 B2
(45) Date of Patent: Apr. 6, 2004

(54) ENDOSCOPE HOLDING APPARATUS

(75) Inventors: Hiroyuki Takase, Tokyo (JP); Teruo Ouchi, Saitama (JP); Satoshi Kidooka, Tokyo (JP)

(73) Assignee: PENTAX Corporation, Tokyo (JP)

( * ) Notice: Subject to any disclaimer, the term of this patent is extended or adjusted under 35 U.S.C. 154(b) by 128 days.

(21) Appl. No.: 10/059,166

(22) Filed: Jan. 31, 2002

(65) Prior Publication Data

US 2002/0123663 A1 Sep. 5, 2002

(30) Foreign Application Priority Data

Feb. 2, 2001 (JP) .................................... P2001-026582
Dec. 26, 2001 (JP) .................................... P2001-393117

(51) Int. Cl.[7] ................................................ A61B 1/00
(52) U.S. Cl. ........................ 600/102; 600/121; 600/124
(58) Field of Search ............................. 600/121, 124, 600/102, 133; 248/176.1; 211/85.15, 78; 383/120

(56) References Cited

U.S. PATENT DOCUMENTS

| | | | | |
|---|---|---|---|---|
| 3,754,370 A | * | 8/1973 | Hanson | 53/459 |
| 3,958,768 A | * | 5/1976 | Fairbanks | 242/595 |
| 5,337,731 A | | 8/1994 | Takahashi et al. | |
| 5,359,991 A | | 11/1994 | Takahashi et al. | |
| 5,520,607 A | * | 5/1996 | Frassica et al. | 600/102 |
| 5,551,945 A | * | 9/1996 | Yabe et al. | 600/122 |
| 5,558,262 A | * | 9/1996 | Simhaee | 225/106 |
| 5,562,602 A | * | 10/1996 | Yabe et al. | 600/121 |
| 5,569,161 A | * | 10/1996 | Ebling et al. | 600/121 |
| 5,674,182 A | * | 10/1997 | Suzuki et al. | 600/129 |
| 5,679,110 A | * | 10/1997 | Hamazaki | 600/124 |
| 5,702,348 A | * | 12/1997 | Harhen | 600/124 |
| 5,706,993 A | * | 1/1998 | DeMatteis | 225/106 |
| 5,935,058 A | * | 8/1999 | Makita et al. | 600/200 |

FOREIGN PATENT DOCUMENTS

JP  2778751  5/1998

* cited by examiner

*Primary Examiner*—Beverly M. Flanagan
(74) *Attorney, Agent, or Firm*—Greenblum & Bernstein, P.L.C.

(57) ABSTRACT

A cover tube, which is formed to be opened only at its upper surface and closed at its remaining portions, is disposed so as to be attachable and detachable beneath a hanger for suspending and holding an endoscope or an endoscope treatment member and so as to surround the tip end portion of the endoscope or the endoscope treatment member in a state of being suspended from and held by the hanger.

8 Claims, 14 Drawing Sheets

1
1a

ENDOSCOPE HOLDING APPARATUS

BACKGROUND OF THE INVENTION

The present invention relates to an endoscope holding apparatus for suspending and holding an endoscope or an endoscopic treatment member.

Each of an endoscope and an endoscopic treatment member is generally configured in a manner that an operation portion is coupled to the base end of an elongated insertion portion. Thus, in most cases, each of the endoscope and the endoscopic treatment member is held in a state where the operation portion is hung on a hanger and the insertion portion is suspended beneath the operation portion.

However, waste liquid such as exudation within the body is adhered to the endoscope or the endoscopic treatment member as to which an inspection using the endoscope has just finished. Thus, if such an endoscope or an endoscopic treatment member is held in the aforesaid state, there may arise a case that the waste liquid drips on a floor or a person touches or contacts with the waste liquid and is polluted while moving. In contrast, there may arise a case that when a peripheral person or thing contacts with the sterilized endoscope or endoscopic treatment member before use, the endoscope or the endoscopic treatment member is polluted.

SUMMARY OF THE INVENTION

Accordingly, an object of the invention is to provide a sanitary endoscope holding apparatus which is arranged in a manner that the periphery is hardly polluted by an endoscope or an endoscopic treatment member suspended from a hanger and, on the contrary, the endoscope or the endoscopic treatment member hardly contacts with a peripheral thing or person and is polluted.

In order to attain the aforesaid object, an endoscope holding apparatus according to the present invention is designed such that a cover tube, which is formed to be opened only at it's upper surface and closed at its remaining portions, is disposed so as to be attachable and detachable beneath a hanger for suspending and holding the endoscope or an endoscopic treatment member and so as to surround at least a tip end portion of the endoscope or the endoscopic treatment member in a state of being suspended from and held by the hanger.

The hanger may be attached to a proximity of an upper end of a pillar, and a cover tube holding member for holding the cover tube may be attached to the pillar beneath the hanger. In case that an attachment height of the cover tube holding member with respect to the pillar is adjustable, the apparatus can be adapted for various kinds of endoscopes.

The cover tube may be formed by a soft bag-shaped member. A plurality of the cover tubes may be disposed in a state that the cover tubes are jointed in series and wound into a rolled shape, and the cover tube pulled down from the rolled shape may be disposed to surround the at least the tip end portion of the endoscope or endoscopic treatment member suspended from and held by the hanger. In this case, the supply of the cover tube is easy.

Further, in this case, the cover tube holding member may have a rolled portion support portion for rotatably supporting the rolled shape of the cover tubes, and a pull down portion placement portion for placing a proximity of an upper end portion of the cover tube pulled down from the rolled shape thereon, and a cutting member may be provided in the vicinity of the pull down portion placement portion for cutting a joint portion between adjacent ones of the jointed cover tubes.

In case that the cover tube has a pleat extending in a longitudinal direction, and/or an opening of the cover tube extends obliquely with respect to a longitudinal direction of the cover tube, the insertion of the endoscope or endoscopic treatment member into the cover tube can be facilitated.

The cover tube may be a rigid tubular member, and may be extensible in an elevational direction.

The present disclosure relates to the subject matter contained in Japanese patent application Nos. 2001-026582 (filed on Feb. 2, 2001) and 2001-393117 (filed on Dec. 26, 2001), which are expressly incorporated herein by reference in their entireties

DESCRIPTION OF THE PREFERRED EMBODIMENT

The embodiments of the invention will be explained with reference to the accompanying drawings.

Figure 1:
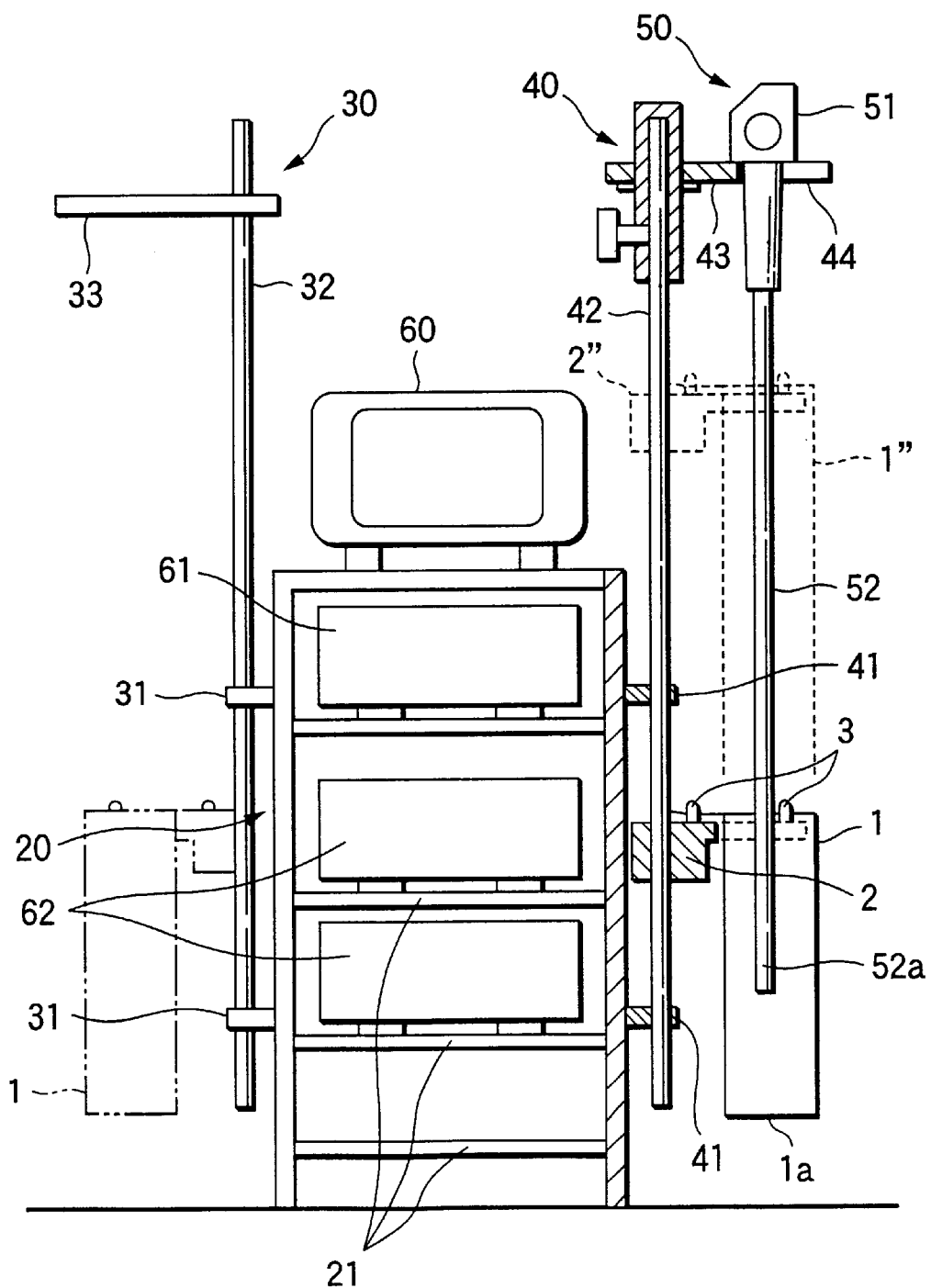
FIG. 1 is a front view of an endoscope system rack to which an endoscope holding apparatus according to the first embodiment of the present invention is attached.

FIG. 1 shows a state where a sterilized endoscope hanger 30 and an unsterilized endoscope hanger 40 are attached to a rack 20 for an endoscope system placed on the floor and an endoscope 50 is suspended from and held by the unsterilized endoscope hanger 40. The endoscope system rack 20 may be configured as a freely movable cart by providing wheels at the bottom portion thereof.

A television monitor 60 for displaying an endoscopically observed image is placed on the top plate of the endoscope system rack 20. A light source device (also serving as a video processor) 61 and peripheral devices 62 such as a video recording apparatus, a suction device etc., for example, used simultaneously with the endoscope 50 are placed beneath the television monitor on a plurality of shelf plates 21 attached at a suitable interval to the rack.

The sterilized endoscope hanger 30 for suspending and holding a sterilized clean endoscope and the unsterilized endoscope hanger 40 for suspending and holding an unsterilized not-clean endoscope are separately attached to the left and right side surfaces of the endoscope system rack 20, respectively.

The endoscope hangers 30, 40 are configured in a manner that the lower half portions of pillars 32, 42 thereof are fixed to fixing members 31, 41 protrusively provided at the side wall surfaces of the endoscope system rack 20 and hanger plates 33, 43 are attached to portions near the upper end portions of the pillars 32, 42, respectively.

A suspension holding groove 44 for hooking the operation portion 51 of the endoscope 50 is formed at the hanger plate 43 of the unsterilized endoscope hanger 40. Since the operation portion 51 is configured in a manner that the upper half portion thereof is larger than the lower half portion thereof, the suspension holding groove 44 is formed to have a size for passing the lower half portion of the operation portion 51 but not passing the upper half portion thereof. The sterilized endoscope hanger 30 has a configuration similar to that of the unsterilized endoscope hanger.

According to such a configuration of the endoscope holding apparatus, when the operation portion 51 of the not-clean endoscope 50 after use is engaged with the hanger plate 43 of the unsterilized endoscope hanger 40, the insertion portion 52 is suspended from the hanger plate and so the endoscope 50 is placed in a state of being entirely suspended from and held by the hanger plate.

A cover tube 1, which is formed to be opened only at its upper surface and closed at its remaining portions, is disposed beneath the hanger plate 43 so as to surround the tip end portion 52a of the insertion portion 52 of the endoscope 50 suspended from and held by the hanger plate 43.

Figure 2:
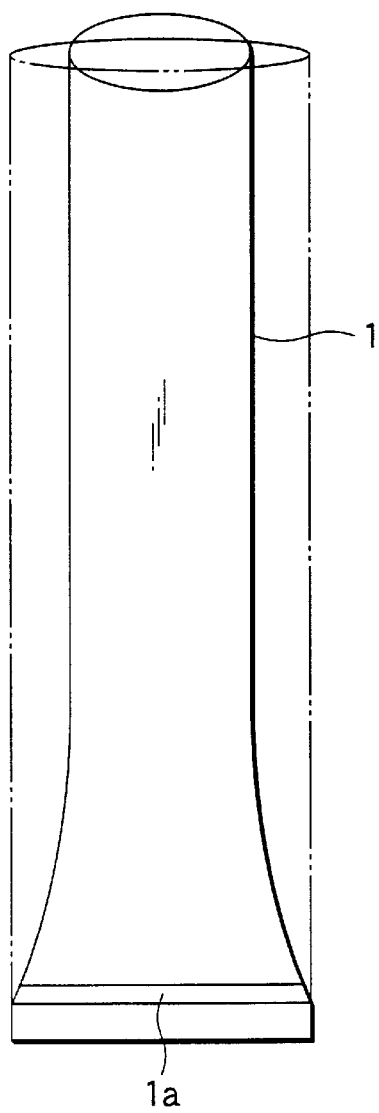
FIG. 2 is a perspective view of a cover tube according to the first embodiment of the invention.

In this embodiment, the cover tube 1 is formed by a soft elongated bag made of polyethylene, for example, as shown as a single element in FIG. 2, and the bottom portion 1a thereof is sealed by the thermal welding etc., so that the cover tube 1 is formed to be opened only at its upper end.

As shown in FIG. 1, the upper end opening portion of the cover tube 1 is attached so as to be freely attachable and detachable to a cover tube holding member 2 fixed to the pillar 42. In this respect, the fixing position of the cover tube holding member 2 with respect to the pillar 42 may be arranged to be adjustable in accordance with the length of the insertion portion 52 of the endoscope 50. Further, the cover tube 1 may be detachably attached to the rack 20, and in this case it is preferable to fix the cover tube holding member 2 directly onto the rack 20, not the pillar 42.

Figure 3:
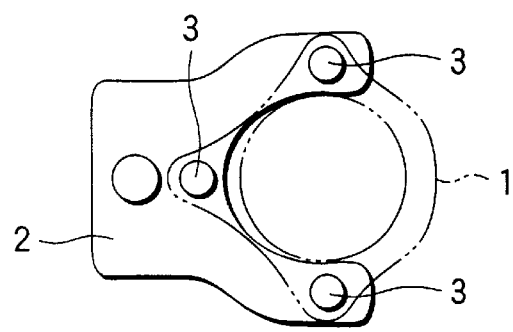
FIG. 3 is a plan view of a cover tube holding member according to the first embodiment of the invention.

An attachment portion, for the cover tube, of the holding member 2 is configured in an almost U-shape, for example, when seen from the upper side as shown in FIG. 3, and a plurality of engaging pins 3 for passing through the cover tube 1 thereby to engage therewith are provided in an upwardly protruding manner at the attachment portion.

Figure 4:
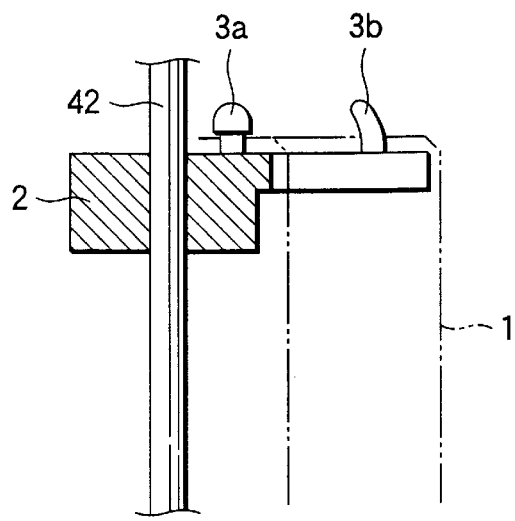
FIG. 4 is a front view of the cover tube holding member according to the first embodiment of the invention.

Each of the engaging pins 3 may be formed in a mushroom shape, for example, as shown by a symbol 3a in FIG. 4 so that the cover tube 1 does not come out of the attachment portion against an operator's intention. Alternatively, each of the engaging pins may be formed in a bent shape in a manner that the upper half portion thereof is directed to the pillar 42 side as shown by a symbol 3b.

In the endoscope holding apparatus according to the embodiment configured in this manner, the tip end portion 52a of the insertion portion 52 of the polluted endoscope 50 being suspended from and held by the hanger 40 can be placed in a state of being surrounded by the cover tube 1.

Thus, the waste liquid etc. dripping from the insertion portion 52 of the endoscope 50 is accumulated within the cover tube 1 and so does no fall on the floor. Further, a person moving around the periphery of the endoscope scarcely touches or contacts directly with the insertion portion 52. The cover tube 1 may be disposed of after using or may be cleaned and used again after using.

As shown by a broken line in FIG. 1, a cover tube holding member 2" may be attached to an upper portion of the pillar 42, and a cover tube 1" long in entire length may be attached to the cover tube holding member 2" so as to surround the half or more or the most of the insertion portion 52 of the endoscope 50.

Further, as shown by an alternate long and two short dashed line in FIG. 1, when another cover tube 1 similar to that provided on the unsterilized endoscope hanger 40 side is disposed beneath the hanger 30, it is possible to prevent the occurrence of such a phenomenon that a sterilized clean endoscope suspended from and held by the sterilized endoscope hanger contacts with a peripheral person or thing and is polluted.

Figure 5:
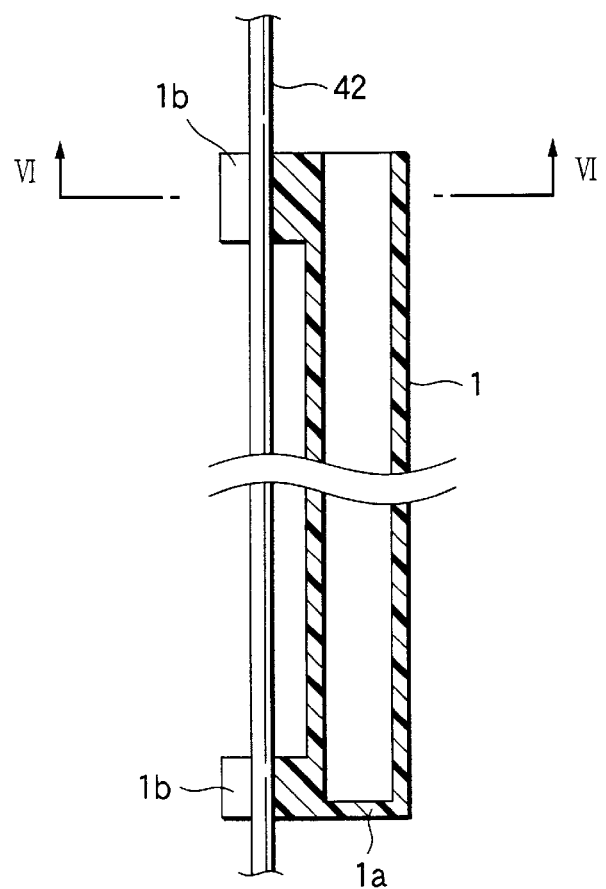
FIG. 5 is a sectional view of the side surface of a cover tube portion according to the second embodiment of the invention.
Figure 6:
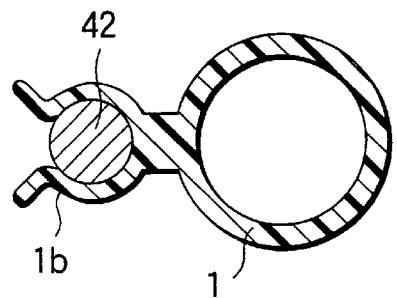
FIG. 6 is a sectional view along a line VI—VI in FIG. 5 in the second embodiment of the invention.

The invention is not limited to the aforesaid embodiment and may be arranged in a manner that the cover tube 1 formed by hard member, for example, is attached in a movable manner to the pillar 42 by using a spring clamp 1b etc. which deforms elastically, for example, as in a second embodiment shown in FIG. 5 and FIG. 6 showing a section along a line VI—VI in FIG. 5.

Figure 7:
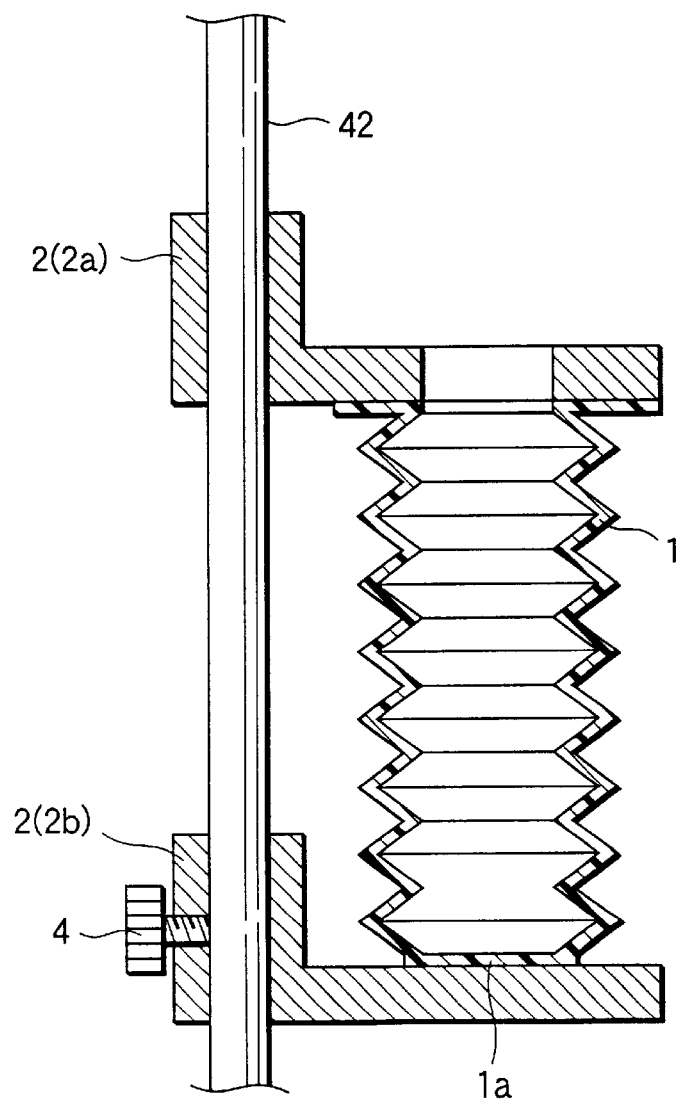
FIG. 7 is a sectional view of the side surface of a cover tube portion according to the third embodiment of the invention.

Further, as in a third embodiment shown in FIG. 7, the cover tube 1 may be formed in a bellows shape freely extensible in an elevational direction, and holding members 2 (2a, 2b) may be attached to the upper and lower ends of the cover tube so as to be movable with respect to the pillar 42, respectively. Reference numeral 4 designates a manually operable fixing screw.

Figure 8:
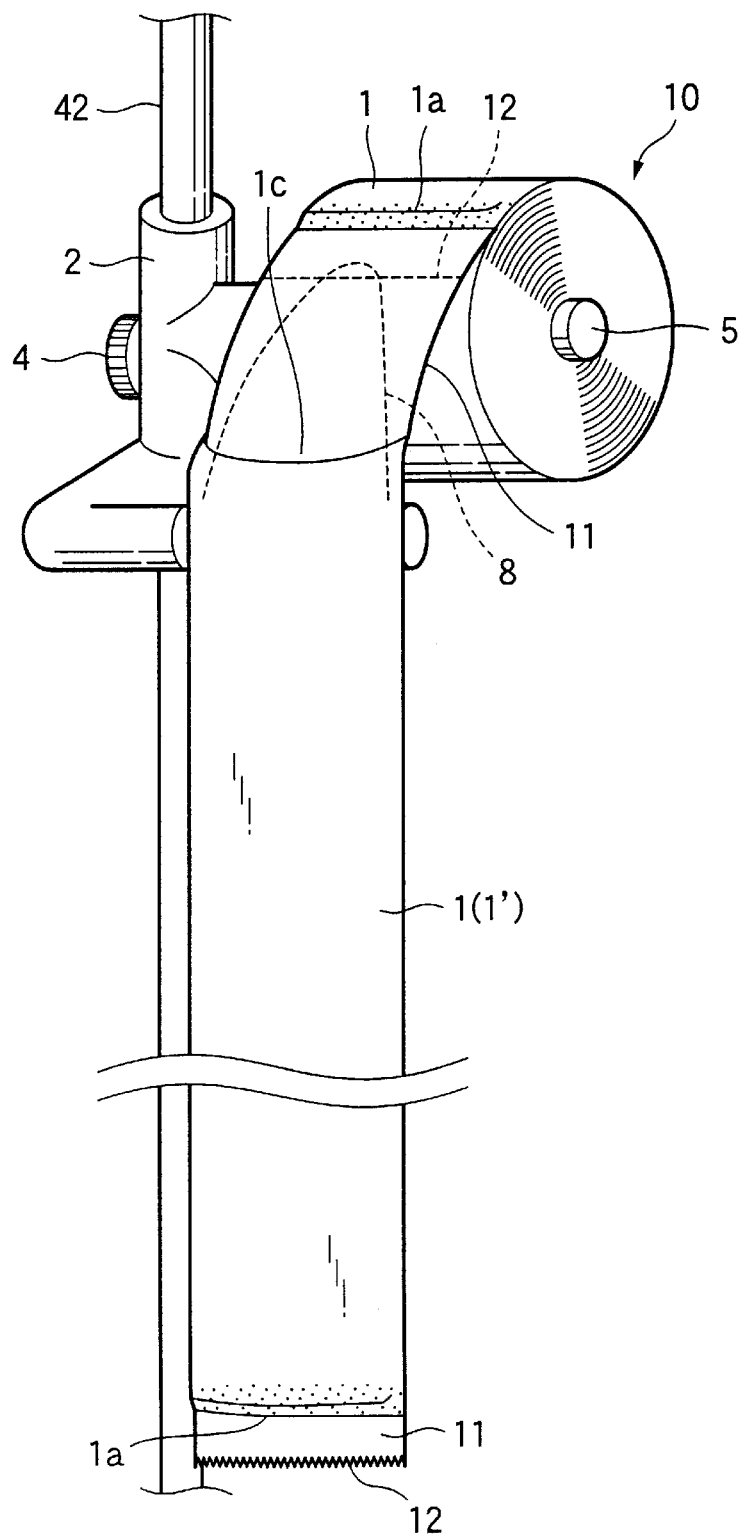
FIG. 8 is a perspective view of a state in which a cover tube is attached to a cover tube holding member according to the fourth embodiment of the invention.
Figure 9:
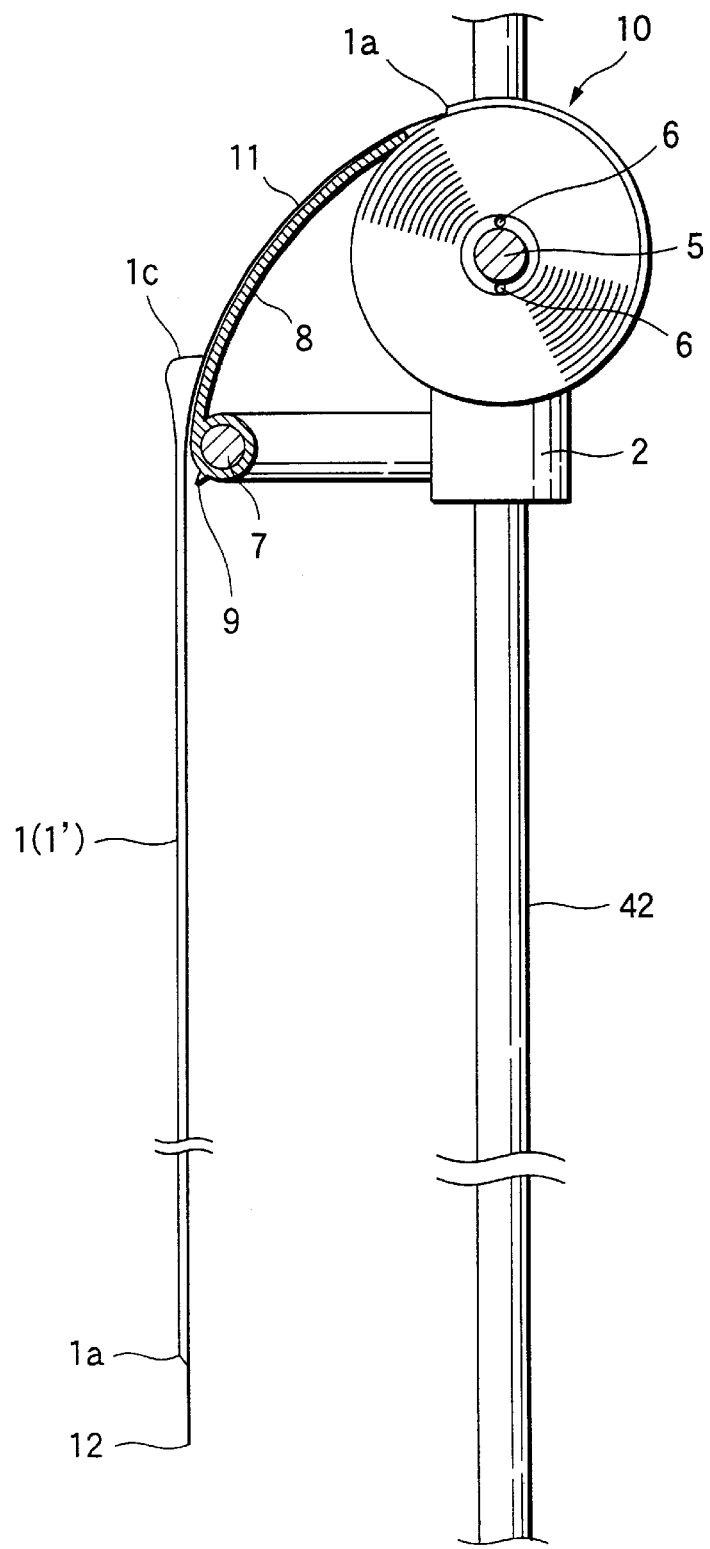
FIG. 9 is a sectional view of the side surface in the state in which the cover tube is attached to the cover tube holding member according to the fourth embodiment of the invention.

FIGS. 8 and 9 show a fourth embodiment of the present invention, wherein a plurality of cover tubes 1 (for example, about 10 to 100 cover tubes), each being formed of a flexible bag member, are disposed such that they are connected in series and wound into a rolled shape.

A pull-down portion 1' of the cover tube 1, which is pulled down from a rolled shaped portion 10 and suspended downwardly, is disposed at a position suitable for insertion of the insertion portion 52 of the endoscope 50 thereinto.

Note that FIGS. 8 and 9 show a state in which the endoscope 50 is not held by the unstarilized endoscope hanger 40.

The cover tube holding member 2 has a rolled portion support shaft 5 for holding the rolled shape portion 10 to be rotatable about an axis thereof, and a placement tongue piece 8 for placing the proximity of the upper end portion of the pull-down portion 1' of the cover tube 1 thereon.

The cover tube holding member 2 is slidably attached to the pillar 42 beneath the unsterilized endoscope hanger 40, and can be fixed thereto at any arbitrary position using the manually operable fixing screw 4.

To manufacture the plurality of cover tubes 1 wound in the rolled shape, a single, continuous, long and flexible bag member is formed of polyethylene terephthalate (PET) resin or the like, and then a portion serving as a bottom portion 1a of each cover tube 1 is sealingly closed by thermal welding.

Thereafter, an upper end opening 1c of an adjacent cover tube 1 is formed while securing a predetermined distance from the bottom portion 1a to provide a joint portion 11. The surface around the upper end opening 1c of the cover tube 1 may be formed as a rough surface or embossing surface to facilitate the opening of the upper end opening 1c during the use.

Each of the joint portions 11 is formed with sewing cuts 12 extending in a direction substantially perpendicular to the longitudinal direction and being located close to the bottom portion 1a so that the joint portion 11 can be readily cut along the sewing cuts 12.

Figure 10:
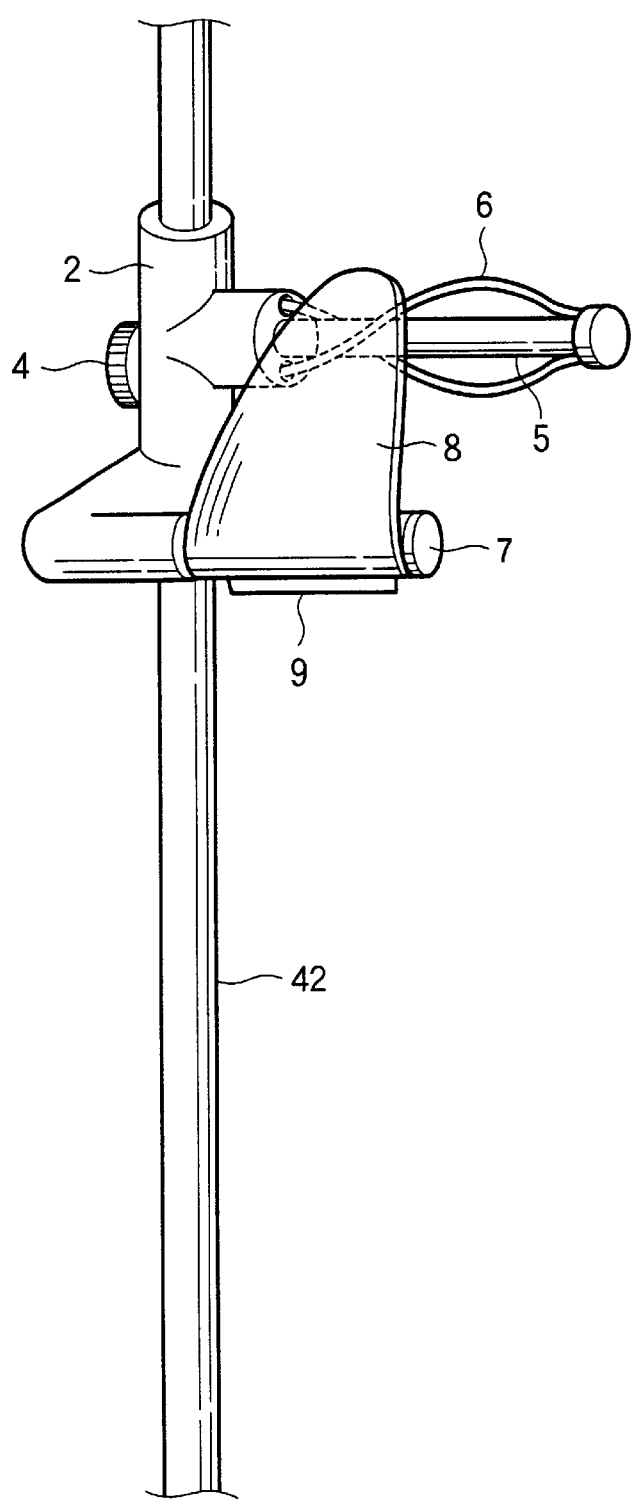
FIG. 10 is a perspective view of the cover tube holding member according to the fourth embodiment of the invention.
Figure 11:
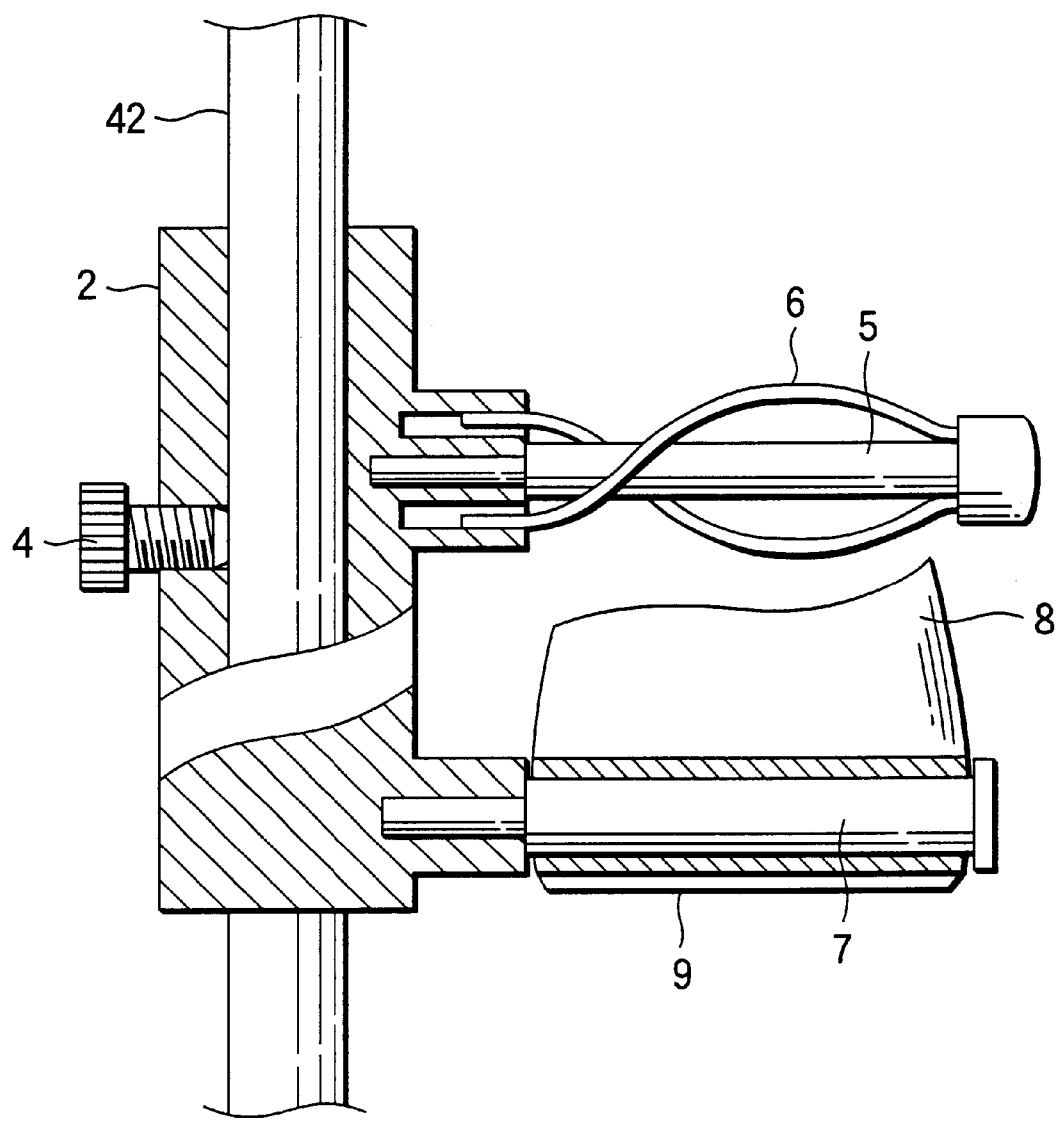
FIG. 11 is a sectional view of the front surface, showing combined sections of the cover tube holding member according to the fourth embodiment of the invention.

As illustrated in FIGS. 10 and 11 showing a state in which the cover tube 1 is not attached to the cover tube holding member 2, the rolled portion support shaft 5 loosely insertable into an axial hole of the rolled shape portion 10 is protruded laterally of the cover tube holding member 2, and a plurality of spring wires 6 for applying suitable friction against the rotation of the rolled shape portion 10 are attached to surround the rolled portion support shaft 5.

The placement tongue piece 8 is formed as a tongue-like configuration gently curved to smoothly suspend the pull-down portion 1' from the rolled shape portion 10 of the cover tube 1 therealong. The lower end portion of the placement tongue piece 8 is rotatably fitted on a tongue piece support shaft 7 protruded from the cover tube holding member 2 to be in parallel to the rolled portion support shaft 5 at a location obliquely below the rolled portion support shaft 5.

The placement tongue piece 8 is narrower in width than the cover tube 1 so as not to be polluted by the insertion portion 52 of the endoscope 50, and has a cutting edge 9 that is slightly protruded downwardly from the lower end portion thereof to be abutted against the sewing cuts 12 to thereby cut the joint portion 11.

Consequently, in a state in which the cover tube 1 is set on the cover tube holding member 2, as shown in FIG. 9, the joint portion 11, located at the upper end of the pull-down portion 1' pulled down from the rolled shape portion 10, is placed on the placement tongue piece 8, and the pull-down portion 1' is suspended therefrom, so that the upper end opening 1c is located slightly above the lower end of the placement tongue piece 8, and the cutting edge 9 is located behind and concealed by the pull-down portion 1'.

Figure 12:
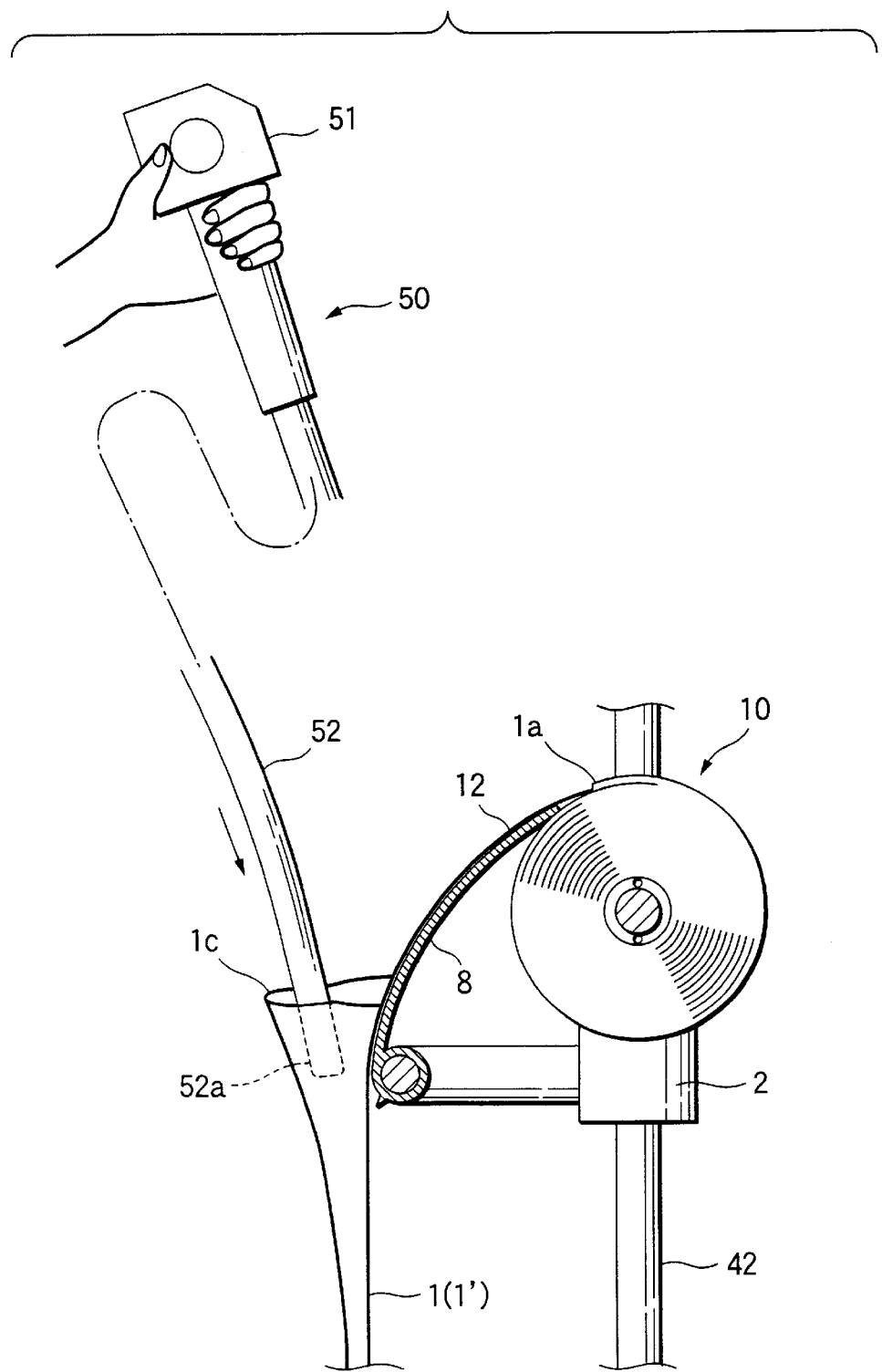
FIG. 12 is a side surface view, showing, partially in section, a state in which an insertion portion of an endoscope is inserted into the cover tube according to the fourth embodiment of the invention.
Figure 13:
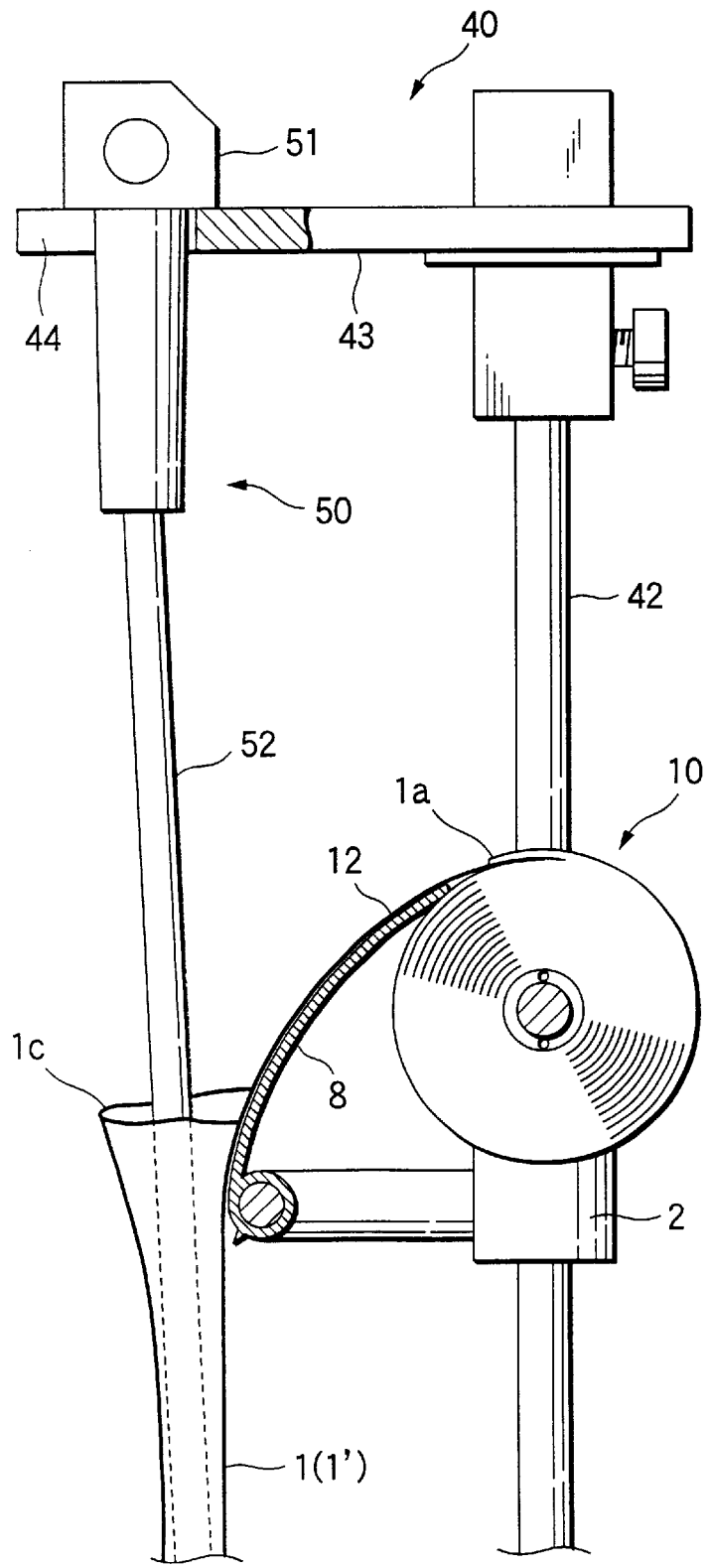
FIG. 13 is aside surface view, showing, partially in section, a state in which the endoscope is suspended on an unsterilized endoscope hanger according to the fourth embodiment of the invention.

When the polluted endoscope 50 after the use is suspended on the unsterilized endoscope hanger 40, as shown in FIG. 12, the upper end opening 1c of the pull-down portion 1' of the cover tube 1 is opened slightly largely with a finger tip or the like, and then the insertion portion 52 of the endoscope 50 is inserted into the cover tube 1 from the leading end portion 52a thereof, and thereafter, as shown in FIG. 13, the operation portion 51 is engaged with the hanger plate 43 of the unsterilized endoscope hanger 40.

In handling as mentioned above, since the upper end opening 1c of the pull-down portion 1' of the cover tube 1 and the sewing cuts 12 to be cut are sufficiently remote one from another, a cover tube 1 to be pulled-down next from the rolled shape portion 10 is prevented from being polluted by the insertion portion 52 of the endoscope 50 and therefore kept clean.

Figure 14:
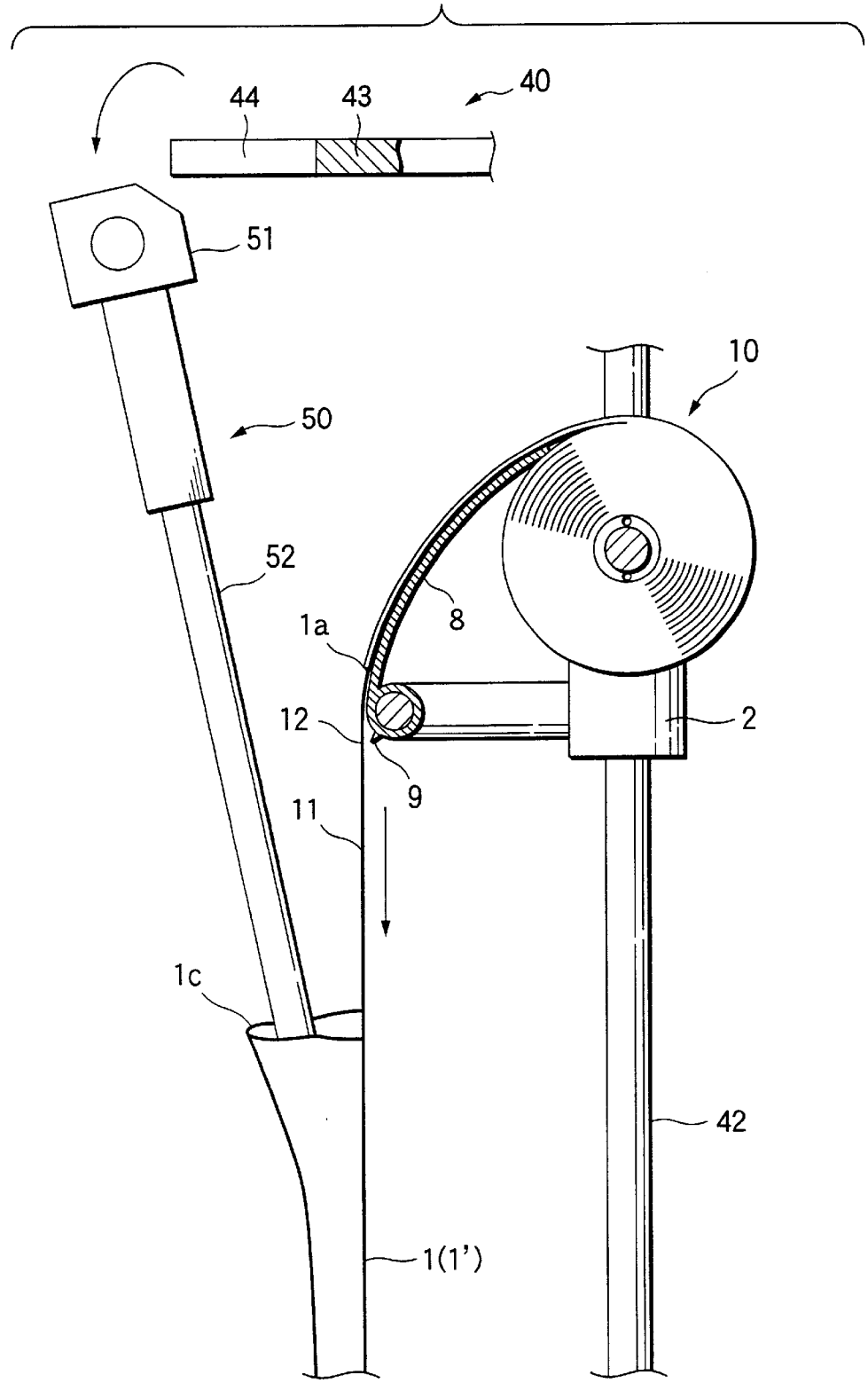
FIG. 14 is a side surface view, showing, partially in section, a state in which the endoscope is removed from the unsterilized endoscope hanger according to the fourth embodiment of the invention.

When the endoscope 50 is detached from the unsterilized endoscope hanger 40, as shown in FIG. 14, the operation portion 51 is disengaged from the hanger plate 43 of the unsterilized endoscope hanger 40 and pulled down slightly to be stopped at such a position that the sewing cuts 12 formed in the joint portion 11 of the cover tube 1 are located in opposition to the cutting edge 9.

Figure 15:
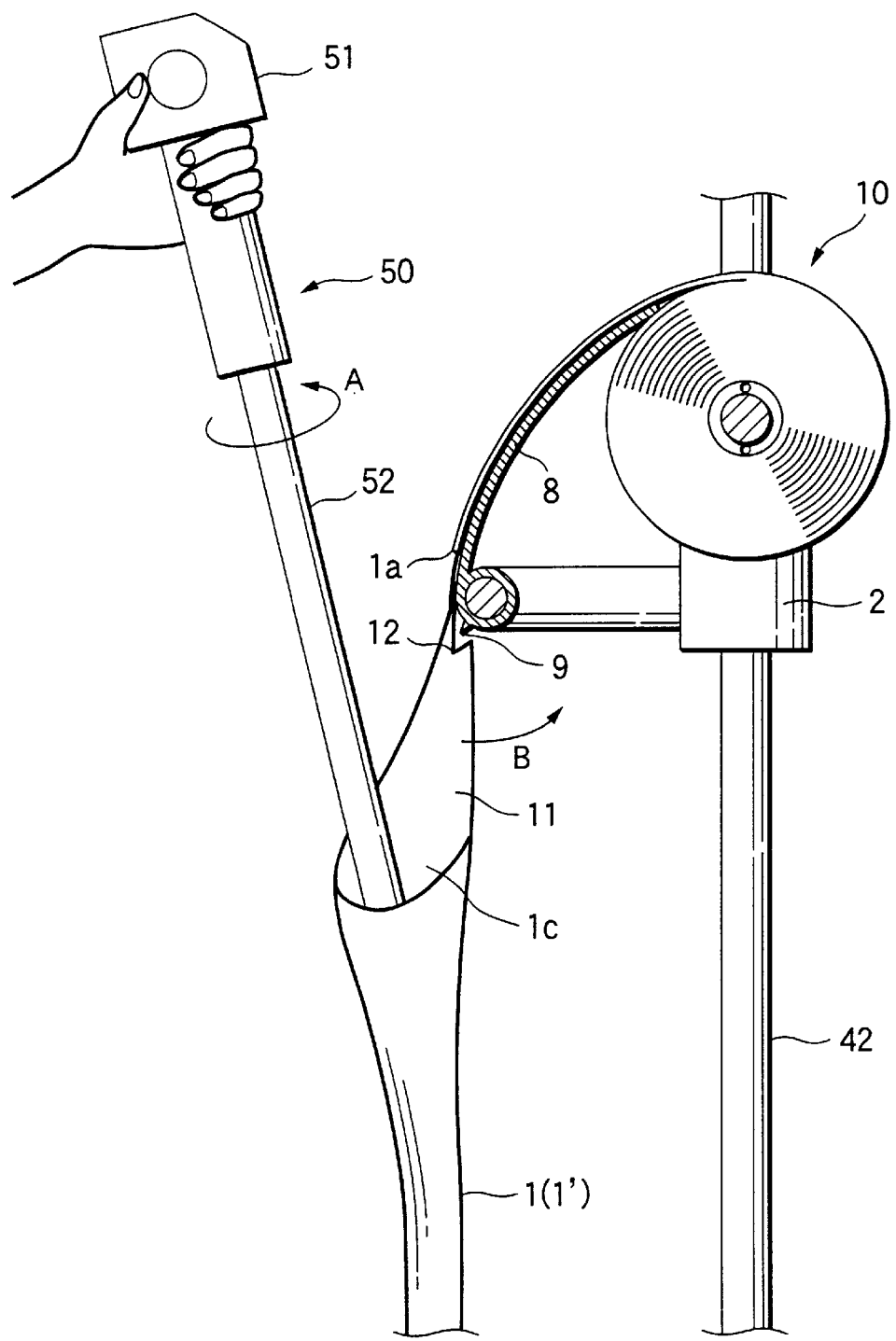
FIG. 15 is a side surface view, showing, partially in section, a state in which a joint portion of the cover tube is cut according to the fourth embodiment of the invention.

Then, as shown in FIG. 15, the endoscope is rotated slightly largely as indicated by an arrow A, the sewing cuts 9 are abutted against the cutting edge 9 sequentially from the lateral end thereof so that the joint portion 11 is cut along the sewing cuts 9.

Accordingly, the polluted endoscope 50 can be detached from the hanger and carried in a state the insertion portion 52 thereof is kept surrounded by the cover tube 1. A next cover tube 1 can be ready for the use if the cover tube 1 is pulled down from the rolled shape portion 10 to establish the setting state shown in FIG. 9. Accordingly, the cover tubes 1 can be readily replaced and used one by one correspondingly to the number of the cover tubes 1 wound into the rolled shape portion 10.

Figure 16:
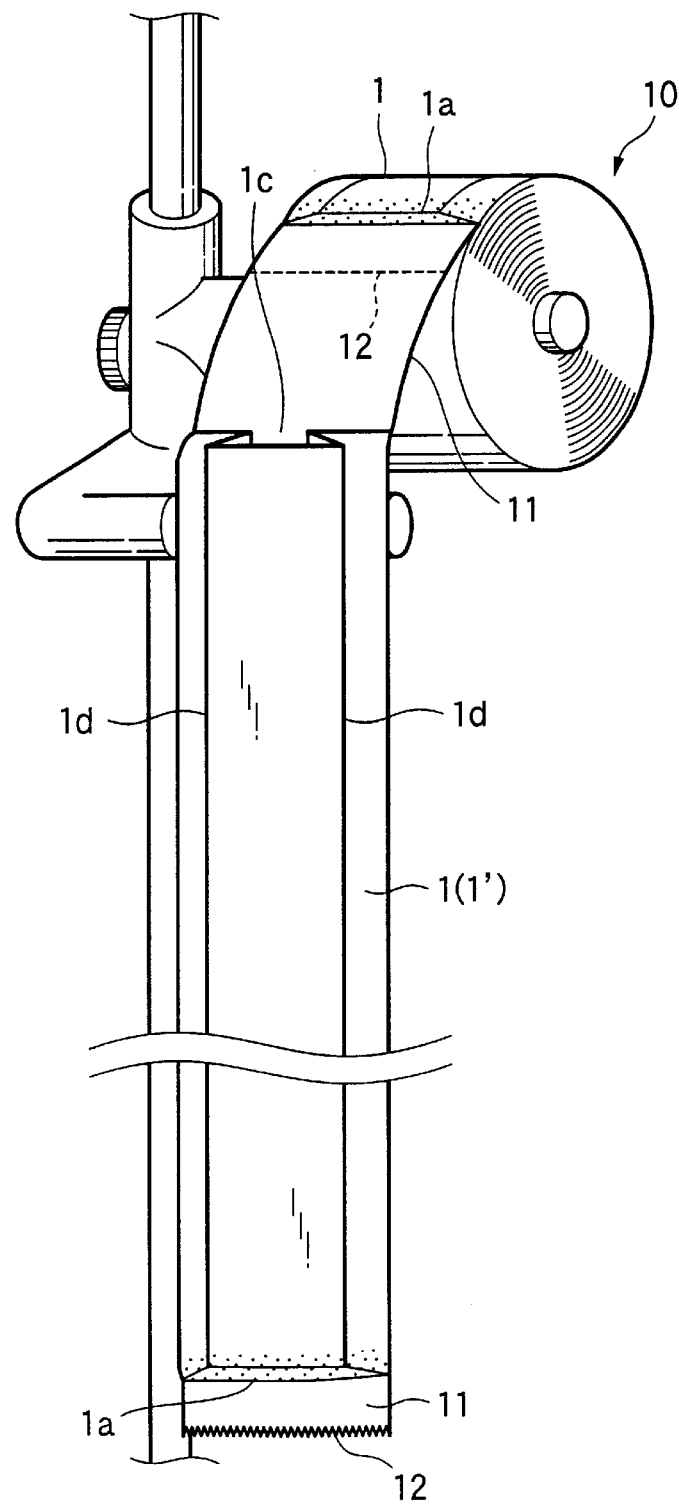
FIG. 16 is a perspective view showing a state in which a cover tube is attached to a cover tube holding member according to the fifth embodiment of the invention.

FIG. 16 shows a fifth embodiment of the present invention, wherein pleats 1d are formed in the cover tube 1 to extend in the longitudinal direction thereof. This arrangement makes it possible to readily open the upper end opening 1c largely to thereby facilitate the insertion of the insertion portion 52 of the endoscope 50. An example in which two pleats 1d are provided is illustrated in FIG. 16, but a single pleat 1d may be provided, or otherwise, three or more pleats 1d may be provided.

Figure 17:
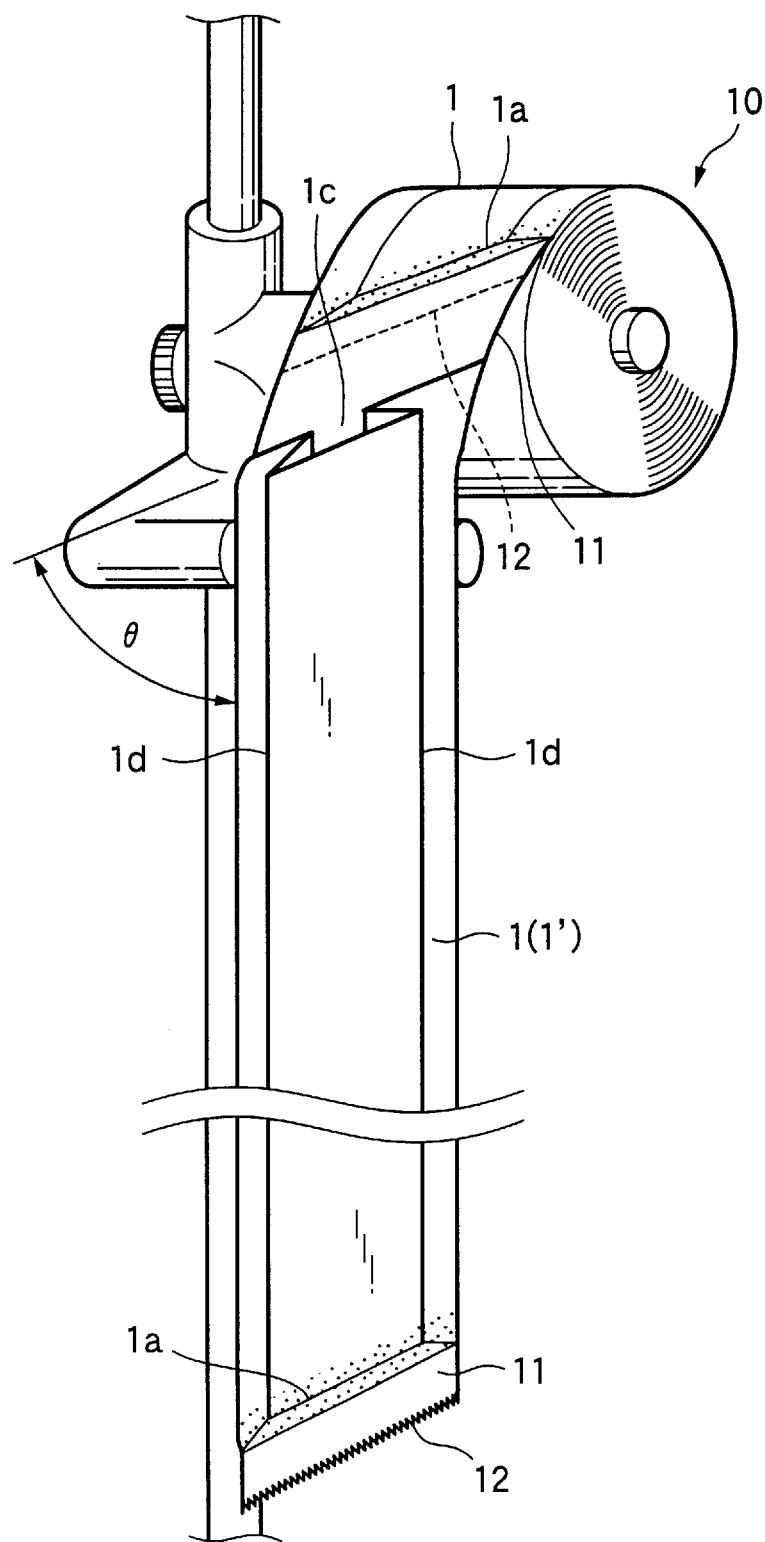
FIG. 17 is a perspective view showing a state in which a cover tube is attached to a cover tube holding member according to the sixth embodiment of the invention.

FIG. 17 shows a sixth embodiment of the present invention, wherein the upper end opening 1c of the cover tube 1 is formed obliquely with respect to the longitudinal direction. This arrangement also facilitate the insertion of the insertion portion 52 of the endoscope 50, and the oblique angle θ preferably fall within a range of, for example, about 30 to 75 degrees (more preferably, about 45 to 60 degrees).

The arrangement of the pleats 1d shown in FIG. 16 and/or the arrangement of the obliquely inclined upper end opening 1c shown in FIG. 17 may be applied to the embodiment using the single cover tube 1 as shown in FIG. 1.

The invention may also be applied to a treatment member holding apparatus for holding an endoscopic treatment member in the same manner as the aforesaid case for holding the endoscope 50.

As described above, according to the invention, the waste liquid etc. dripping from the insertion portion of the endoscope treatment member after use is accumulated within the cover tube and so the waste liquid etc. can be prevented from falling on the floor. Further, since such a possibility that a peripheral thing or person directly touches the endoscope or the treatment member suspended from the hanger becomes small, the peripheral pollution can be prevented. Furthermore, the endoscope or the treatment member suspended from the hanger can be made hardly polluted.

What is claimed is:

1. In an endoscope holding apparatus, a cover tube, which is formed to be opened only at its upper surface and closed at its remaining portions, is disposed so as to be attachable and detachable beneath a hanger for suspending and holding the endoscope or an endoscopic treatment member and so as to surround at least a tip end portion of the endoscope or the endoscopic treatment member in a state of being suspended from and held by the hanger;

wherein a plurality of the cover tubes are disposed in a state that the cover tubes are jointed in series and wound into a rolled shape, and the cover tube pulled down from the rolled shape is disposed to surround at least the tip end portion of the endoscope or endoscopic treatment member suspended from and held by the hanger.

2. The endoscope holding apparatus according to claim 1, wherein the hanger is attached to a proximity of an upper end of a pillar, and a cover tube holding member for holding the cover tube is attached to the pillar beneath the hanger.

3. The endoscope holding apparatus according to claim 2, wherein an attachment height of the cover tube holding member with respect to the pillar is adjustable.

4. The endoscope holding apparatus according to claim 1, wherein the cover tube is formed by a soft bag-shaped member.

5. The endoscope holding apparatus according to claim 1, wherein the cover tube holding member includes a rolled portion support portion for rotatably supporting the rolled shape of the cover tubes, and a pull down portion placement portion for placing a proximity of an upper end portion of the cover tube pulled down from the rolled shape thereon.

6. The endoscope holding apparatus according to claim 5, wherein a cutting member is provided in the vicinity of the pull down portion placement portion for cutting a joint portion between adjacent ones of the jointed cover tubes.

7. The endoscope holding apparatus according to claim 1, wherein the cover tube has a pleat extending in a longitudinal direction.

8. The endoscope holding apparatus according to claim 1, wherein an opening of the cover tube extends obliquely with respect to a longitudinal direction of the cover tube.

* * * * *